(12) United States Patent
Cain et al.

(10) Patent No.: US 8,720,445 B2
(45) Date of Patent: May 13, 2014

(54) TRACHEAL TUBE WITH COLORIMETRIC $CO_2$ INDICATOR

(75) Inventors: Brian Cain, Piedmont, CA (US); Janice Cain, Piedmont, CA (US); Fred Johnson, Pleasanton, CA (US); Steve Woodard, Cupertino, CA (US); Stephen Lee, San Jose, CA (US); Sherry Zhang, Sunnyvale, CA (US)

(73) Assignee: Affirm Medical Technologies, LLC, Petaluma, CA (US)

( * ) Notice: Subject to any disclaimer, the term of this patent is extended or adjusted under 35 U.S.C. 154(b) by 1149 days.

(21) Appl. No.: 12/139,136

(22) Filed: Jun. 13, 2008

(65) Prior Publication Data

US 2009/0095290 A1    Apr. 16, 2009

Related U.S. Application Data

(60) Provisional application No. 60/934,697, filed on Jun. 15, 2007, provisional application No. 60/991,166, filed on Nov. 29, 2007.

(51) Int. Cl.
| | |
|---|---|
| *A61M 16/00* | (2006.01) |
| *A62B 9/06* | (2006.01) |
| *A62B 7/00* | (2006.01) |
| *A62B 9/00* | (2006.01) |

(52) U.S. Cl.
USPC ................................ 128/207.14; 128/205.23

(58) Field of Classification Search
USPC ............. 128/205.23, 207.14–207.17, 200.26; 600/532, 353, 133; 604/171, 199
See application file for complete search history.

(56) References Cited

U.S. PATENT DOCUMENTS

| | | | | |
|---|---|---|---|---|
| 3,373,735 | A | * | 3/1968 | Gallagher ...................... 600/581 |
| 3,402,717 | A | * | 9/1968 | Doherty ................... 128/207.15 |
| 4,728,499 | A | | 3/1988 | Fehder |
| 4,790,327 | A | * | 12/1988 | Despotis ....................... 600/532 |
| 4,879,999 | A | | 11/1989 | Leiman et al. |
| 4,994,117 | A | | 2/1991 | Fehder |
| 5,005,572 | A | * | 4/1991 | Raemer et al. ........... 128/207.14 |
| 5,156,159 | A | | 10/1992 | Lampotang |

(Continued)

FOREIGN PATENT DOCUMENTS

| | | | |
|---|---|---|---|
| GB | 2424190 A | * | 9/2006 |
| WO | WO9511716 | | 5/1995 |
| WO | WO2008157396 | | 12/2008 |

OTHER PUBLICATIONS

Zhang, Fall 2006, SAMPE, Fall 2006, p. 5 (see http://www.arlonstd.com/Library/Guides/D116%20Haibing%20Zhang%20et%20%20al.pdf).*

*Primary Examiner* — Lynne Anderson
*Assistant Examiner* — Bradley Philips
(74) *Attorney, Agent, or Firm* — Bozicevic, Field & Francis LLP; Bret E. Field; Benjamin C. Pelletier

(57) ABSTRACT

Tracheal tubes having an integrated calorimetric $CO_2$ indicator are provided. In certain embodiment, the integrated $CO_2$ indicator is selectively sealed from the remainder of the tracheal tube by a removable sterilization barrier. Also provided are $CO_2$ indicators that exhibit long lasting, breath-to-breath dynamic color change and are storage stable. The devices and compositions of the invention find use in a variety of applications, e.g. in emergent intubation of a subject. Also provided are methods of making the devices and compositions, as well as kits that include the devices and/or compositions of the invention.

28 Claims, 12 Drawing Sheets

(56) References Cited

U.S. PATENT DOCUMENTS

| | | |
|---|---|---|
| 5,166,075 A | 11/1992 | Fehder |
| 5,179,002 A | 1/1993 | Fehder |
| 5,273,029 A | 12/1993 | Wilk et al. |
| 5,456,249 A | 10/1995 | Kirk |
| 5,472,668 A * | 12/1995 | Mills et al. ............ 422/425 |
| 5,517,985 A | 5/1996 | Kirk et al. |
| 5,679,884 A | 10/1997 | Kirk |
| 5,965,061 A * | 10/1999 | Larsson et al. ......... 252/408.1 |
| 6,123,075 A | 9/2000 | Kirk |
| 6,427,687 B1 | 8/2002 | Kirk |
| 6,436,347 B1 | 8/2002 | Cedeon |
| 6,584,974 B1 | 7/2003 | Ratner |
| 6,677,159 B1 * | 1/2004 | Mallow ............ 436/133 |
| 6,709,403 B1 | 3/2004 | Ratner |
| 6,843,250 B2 | 1/2005 | Efrati |
| 6,929,008 B2 * | 8/2005 | Geist ............ 128/205.23 |
| 7,140,370 B2 * | 11/2006 | Tresnak et al. ......... 128/207.14 |
| 2006/0216828 A1 * | 9/2006 | Ratner et al. ............ 436/68 |

* cited by examiner

FIG. 4A
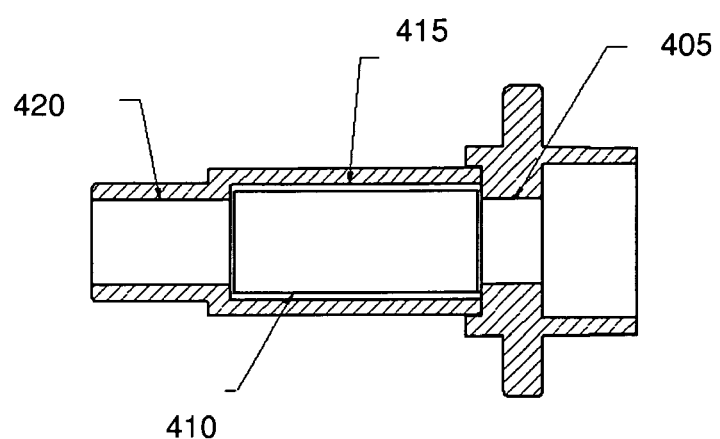
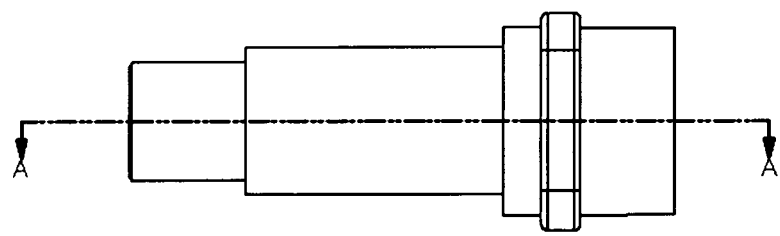
FIG. 4B

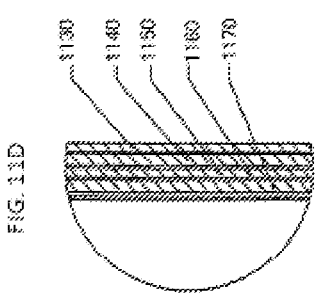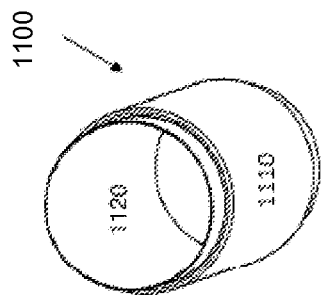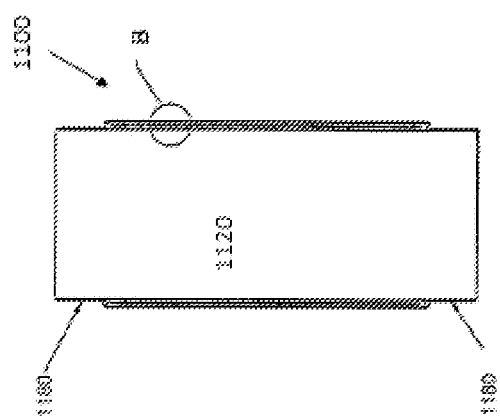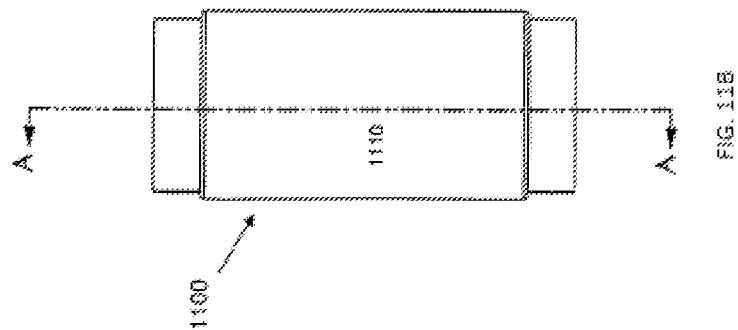

TRACHEAL TUBE WITH COLORIMETRIC $CO_2$ INDICATOR

CROSS-REFERENCE TO RELATED APPLICATIONS

Pursuant to 35 U.S.C. §119 (e), this application claims priority to the filing date of U.S. Provisional Patent Application Ser. No. 60/934,697 filed Jun. 15, 2007 and to the filing date of U.S. Provisional Application Ser. No. 60/991,166 filed Nov. 29, 2007; the disclosures of which applications are herein incorporated by reference.

INTRODUCTION

Accurate detection of $CO_2$ in gaseous samples can be of great importance in the medical field, particularly when attempting to confirm the proper placement of an endotracheal tube in the airway of a patient. A critical step in the intubation of a patient is the determination that the breathing tube or endotracheal tube is placed in the trachea and not in the esophagus. When the tube is correctly placed in the trachea, $CO_2$ will be present in the expired air in concentrations from about 4.5-5.0%. If the tube is in the esophagus, there will be essentially no $CO_2$ detected. In emergency situations, when it is likely that less skilled personnel are available, it is important to confirm of the proper initial placement and continuous correct placement in the trachea.

SUMMARY

Tracheal tubes having an integrated calorimetric $CO_2$ indicator are provided. In certain embodiment, the integrated $CO_2$ indicator is selectively sealed from the remainder of the tracheal tube by a removable sterilization barrier. Also provided are $CO_2$ indicators that exhibit long lasting, breath-to-breath dynamic color change and are storage stable. The devices and compositions of the invention find use in a variety of applications, e.g. in emergent intubation of a subject. Also provided are methods of making the devices and compositions, as well as kits that include the devices and/or compositions of the invention.

BRIEF DESCRIPTION OF THE DRAWINGS

FIGS. 4A & B shows a diagram of a $CO_2$ indicator device with a varying diameter flow chamber in accordance with an embodiment of the present invention.

FIGS. 11A to 11D provide various views of an embodiment of the indicator which is present in a gas permeable, sealed structure.

DETAILED DESCRIPTION

Figure 1:
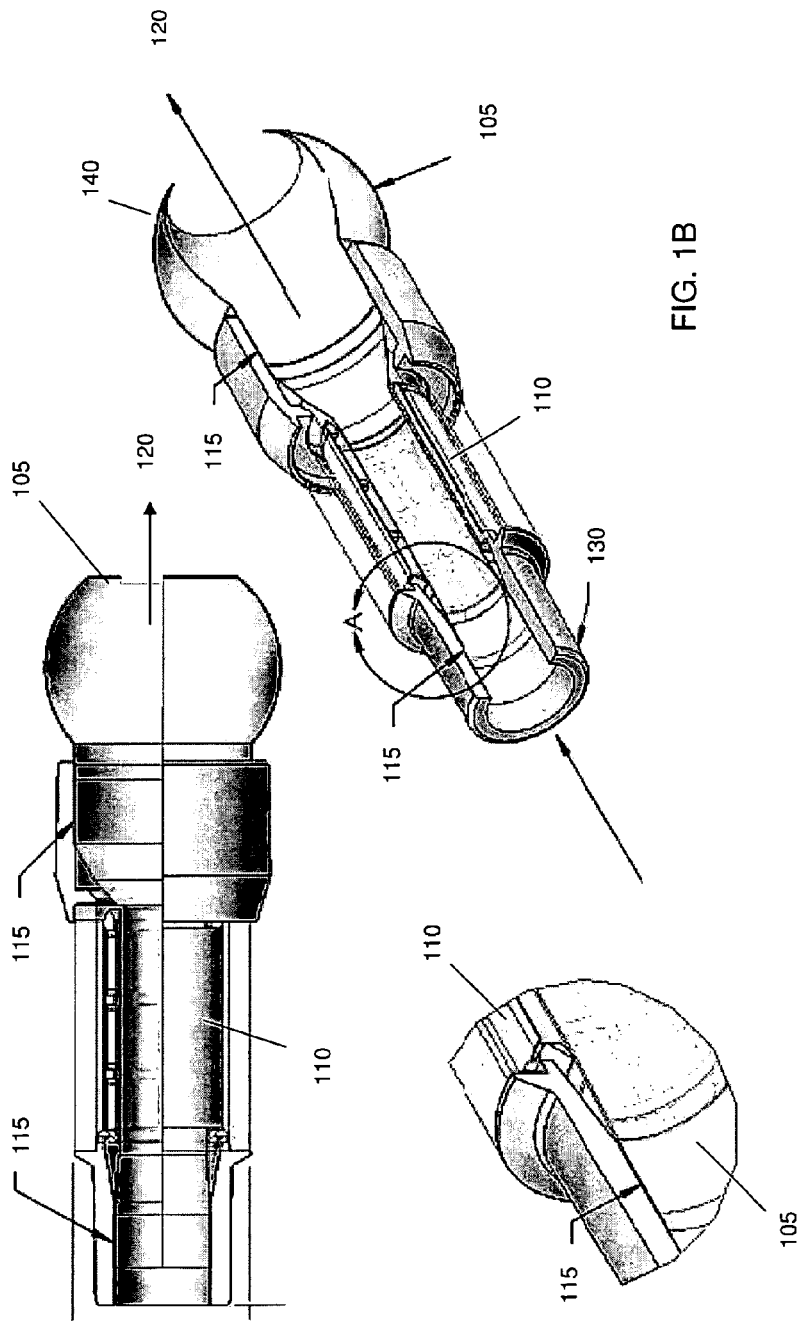
FIGS. 1A-C show a diagram of a $CO_2$ detector device having a film of flexible sealing material in accordance with an embodiment of the present invention.

Tracheal tubes having an integrated calorimetric $CO_2$ indicator are provided. In certain embodiment, the integrated $CO_2$ indicator is selectively sealed from the remainder of the tracheal tube by a removable sterilization barrier. Also provided are $CO_2$ indicators that exhibit breath-to-breath dynamic color change and are storage stable. The devices and compositions of the invention find use in a variety of applications, e.g. in emergent intubation of a subject. Also provided are methods of making the devices and compositions, as well as kits that include the devices and/or compositions of the invention.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. In further describing the subject invention, aspects of tracheal tubes according to embodiments of the invention are described first. Next, embodiments of the CO2 indicator compositions of the invention are reviewed in greater detail. Following this, embodiments of applications in which the devices and compositions find use are reviewed, as well as kits for use in such applications.

Tracheal Tube Device

Aspects of the invention include a tracheal tube device integrated with a $CO_2$ indicator. The integrated indicator is selectively sealed from the remainder of the tracheal tube device by a sterilization barrier which allows for sterilization of the device without sterilization of the indicator despite the indicator's integration into the device. By "selectively sealed" is meant that a barrier is present which isolates the indicator component from the remainder of the device and the external environment of the device, such that when the device is placed in a given environment, components of the environment can contact all but the sealed indicator component of the device. The sterilization barrier selectively sealing the $CO_2$ indicator serves to protect it from the sterilization process (e.g. ethylene oxide gas) while allowing the remainder of the device to be sterilized.

By selectively sealing the $CO_2$ indicator, the tracheal tube and the $CO_2$ indicator can be made and packaged as one integrated device. By providing a removable sterilization barrier, the integrated tracheal tube device can be configured to be opened with one motion, saving valuable time in an emergency. The barrier surrounding the $CO_2$ indicator can be any convenient configuration, such as a film or an internal plug. The $CO_2$ indicator portion of the device may be connected to the tracheal tube portion in such a way that a continuous lumen is formed from one end of the device to the other, allowing the passage of a suction tube, stylet, or analogous structure through the indicator. This "in-line" design of the $CO_2$ indicator can provide the additional benefit of a minimal amount of "dead" space, which can be important in maximizing the efficiency of gas exchange.

By "tracheal tube" is meant any tube used to provide access to the airway, including an endotracheal tube placed through the mouth, a nasotracheal tube placed into the trachea through the nose, and a tracheostomy tube which is placed into the trachea through a tracheostomy, or opening to the trachea created in the neck. The term "tracheal tube" also includes tubes that can access the trachea, or airway, without actually entering the trachea, e.g., products known in the art under the trade name "LMA", (laryngeal mask airway), which will also be referred to as a laryngeo-pharyngeal airway (LPA). A "tracheal tube device" comprises an elongated tubular element having a distal region and a proximal region, with the distal region configured for placement to access the trachea of a subject, with placement either in the trachea, or near the trachea of a subject, as in the case of a laryngeal mask airway. The proximal region of the tubular element extends outside the subject, configured for connection with any type of ventilation apparatus for ventilating a subject. The tracheal tube device in its distal aspect can be dimensioned to fit at least partially inside the trachea of a subject. In certain embodiments, the tube has an inner diameter ranging from 2 mm to 9.5 mm, such as from 2 mm to 9 mm, and including from 2.5 mm to 9 mm; and an outer diameter ranging from 2.5 mm to 10 mm, such as from 2.5 mm to 9.5 mm, and including from 3 mm to 9.5 mm. In some embodiments, such as with a laryngeo-pharyngeal airway (LPA), the distal end of the tube is dimensioned to fit in the pharynx. The length of the tracheal tube device ranges, in certain embodiments, from 5 cm to 50 cm, such as from about 7 cm to 50 cm, and including from 10 cm to 45 cm.

In certain embodiments, the $CO_2$ indicator is present at the proximal region of the elongated tubular element or tracheal tube device. Aspects of invention include devices where the indicator is present on an inner surface of the proximal region of the tubular element. By "proximal region" is meant in the region of the tracheal tube device which extends outside the subject, which connects with a ventilation bag or system. In certain embodiments, the proximal region of the elongated tubular element where the $CO_2$ indicator is present can be located from 2 cm to 25 cm from the proximal end of the tracheal tube device, including 5 cm to 25 cm, such as 7 cm to 20 cm. By "present on an inner surface" is meant in an area of the tracheal tube device where the $CO_2$ indicator will come in contact with the gas flow of a subject's respiration, whether the gas flow comes in contact with the $CO_2$ indicator on only one side of the detector, or on more than one side or surface of the indicator, including flowing through the detector (e.g. through perforations).

The $CO_2$ indicator can have a transparent portion, or window, for viewing of the $CO_2$ calorimetric indicator during use. Various methods of visualization enhancement for the $CO_2$ indicator are disclosed, including enhanced contrast detection using patterns, and simulated motion or adjunctive motion of the detector, which can also indicate the direction of air flow. Also disclosed are various features which increase the functionality and sensitivity of the $CO_2$ indicator, such as increased surface area of the indicator, and perforations allowing increased air flow in and around the detector. The $CO_2$ indicator portion of the device can also be detachable, for use with another tracheal tube, or for exchange of the $CO_2$ indicator. Aspects of the invention also include $CO_2$ indicators that exhibit a dynamic, rapid response reversible $CO_2$ indication with breath-to-breath sensitivity and storage stability. Also provided are methods of making the $CO_2$ indicator, as well as methods of making the tracheal tube device with the $CO_2$ indicator.

In the broadest sense, the $CO_2$ indicator may be any convenient indicator that is capable of transducing a change in $CO_2$ concentration of a gas contacting the indicator into a detectable change, such as a detectable visual change, e.g., a calorimetric change. $CO_2$ indicators of interest include, but are not limited to, those described in U.S. Pat. Nos. 4,728, 499; 4,879,999; 4,994,117; 5,005,572; 5,156,159; 5,166,075; 5,179,002; 6,436,347; 6,584,974; and U.S. Patent Application Publication No. 2006/02168282; the disclosures of which with respect to $CO_2$ indicator compositions are herein incorporated by reference. Of interest in certain embodiments is the use of the particular $CO_2$ indicators as described below, which exhibit the ability of breath-to-breath dynamic color change.

The subject methods may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients are humans.

Figure 2:
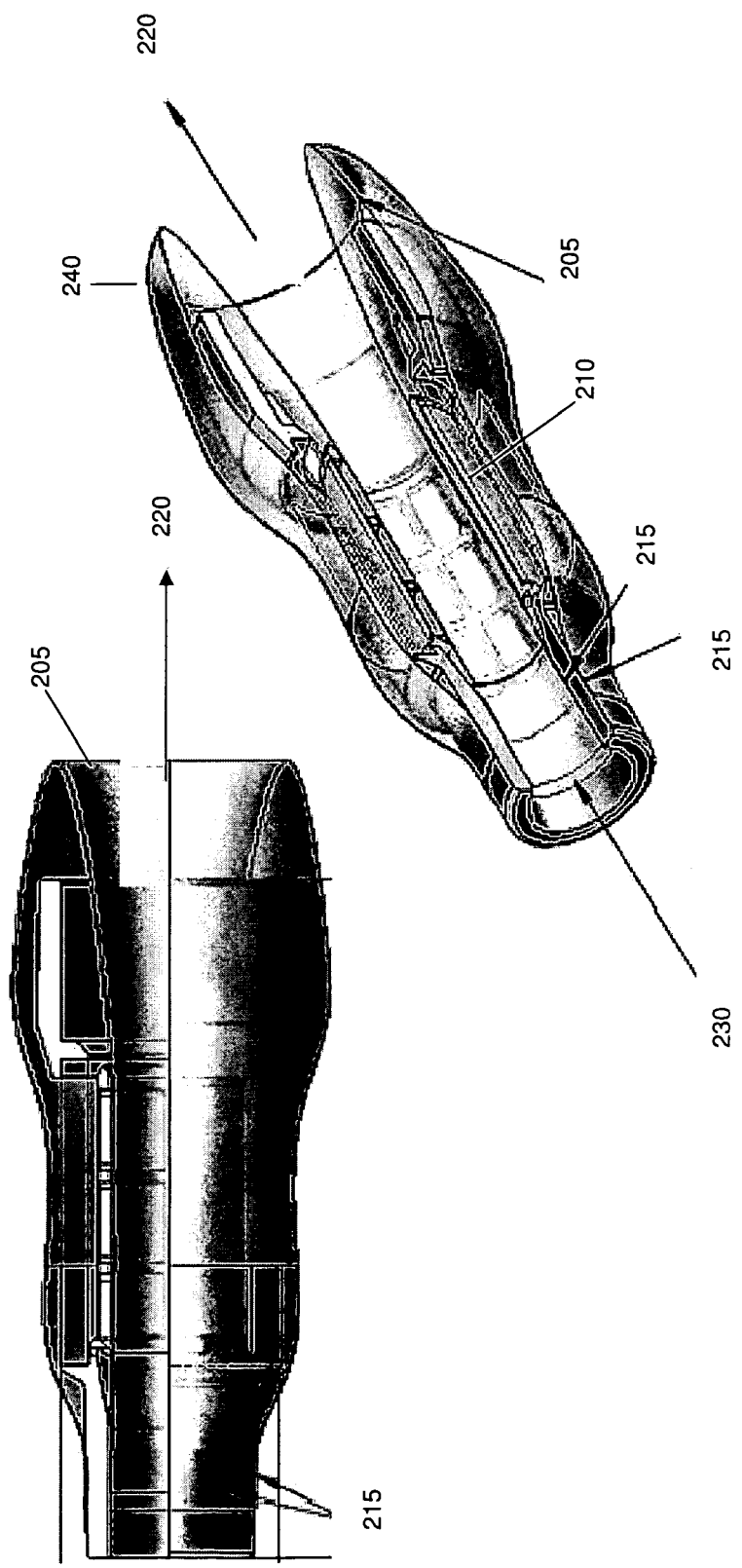
FIG. 2 shows a diagram of a $CO_2$ detector device having a film of flexible sealing material in accordance with an embodiment of the present invention.

Aspects of the invention include a tracheal tube device integrated with a $CO_2$ indicator that is selectively sealed from the remainder of the tracheal tube device by a barrier to allow sterilization of the device. As the indicator is integrated into the device, it is incorporated or built in to the device, as opposed to configurations where it is added on to a device as a separate component. In one embodiment of the invention, the removable sterilization barrier is a film, as shown in FIGS. 1 and 2. In FIGS. 1A-C, a film of flexible sealing material 105 lines the inner lumen of the portion of the device containing the $CO_2$ indicator 110. FIG. 1B shows a cut away view of the device in FIG. 1A, and FIG. 1C shows a detailed view of section A in FIG. 1B. The film barrier inside the $CO_2$ indicator forms sealed areas or surfaces 115 where the film barrier is in contact with the inner diameter of the device both proximal and distal to the $CO_2$ indicator. The flexible sealing material 105 therefore serves as a barrier between the $CO_2$ indicator and the inner lumen of the device which will be exposed to the atmosphere. The seal created by the film barrier serves to protect the $CO_2$ indicator from the sterilization process (e.g. ethylene oxide (EO) gas). The sterilization protocol employed will be one that is compatible with the detector, such that the functionality of the detector is at most only insubstantially altered by the protocol. While any suitable sterilization protocol may be employed, in certain embodiments EO gas sterilization is employed. In FIG. 2, the film of flexible sealing material 205 lines both the inner lumen and the outer surface of the section of the device containing the $CO_2$ indicator 210. The inside and outside portions of the film around the $CO_2$ indicator form sealed areas 215 both proximal and distal to the $CO_2$ indicator, serving as a barrier between the $CO_2$ indicator and the atmosphere.

In both of these embodiments, the film provides a removable sterilization barrier which can be easily removed with one motion, as shown by the directional arrows (120 in FIGS. 1 and 220 in FIG. 2). In these figures, the end of the device closest to the patient that connects to ET tubing is shown as element 130 (FIG. 1) and 230 (FIG. 2), while the end that connects with the ventilator is shown as element 140 (FIG. 1), and 240 (FIG. 2). In one embodiment, the removable sterilization barrier can be integrated with the packaging of the tracheal tube device, such that the process of opening the package can include the removal of the sterilization barrier around the $CO_2$ indicator. In certain embodiments, the barrier film may be removed from the remainder of the device using manual force, e.g., by gripping the film and pulling with only so much force as may be easily provided by an average adult human.

Where the sterilization barrier is a film type barrier such as illustrated in FIGS. 1 and 2 and described above, the barrier may be fabricated from a variety of different types of materials, so long as the material exhibits storage stability, compatibility with the other components of the device and the ability to serve as a sterilization barrier that prevents sterilizing components, e.g., gases, from reaching the indicator composition that is selectively sealed by the barrier. Materials of interest include, but are not limited to, polymeric materials. Suitable polymeric and elastomeric materials of interest include, but are not limited to: butyl rubber, mylar, Teflon, and the like.

Figure 3A:
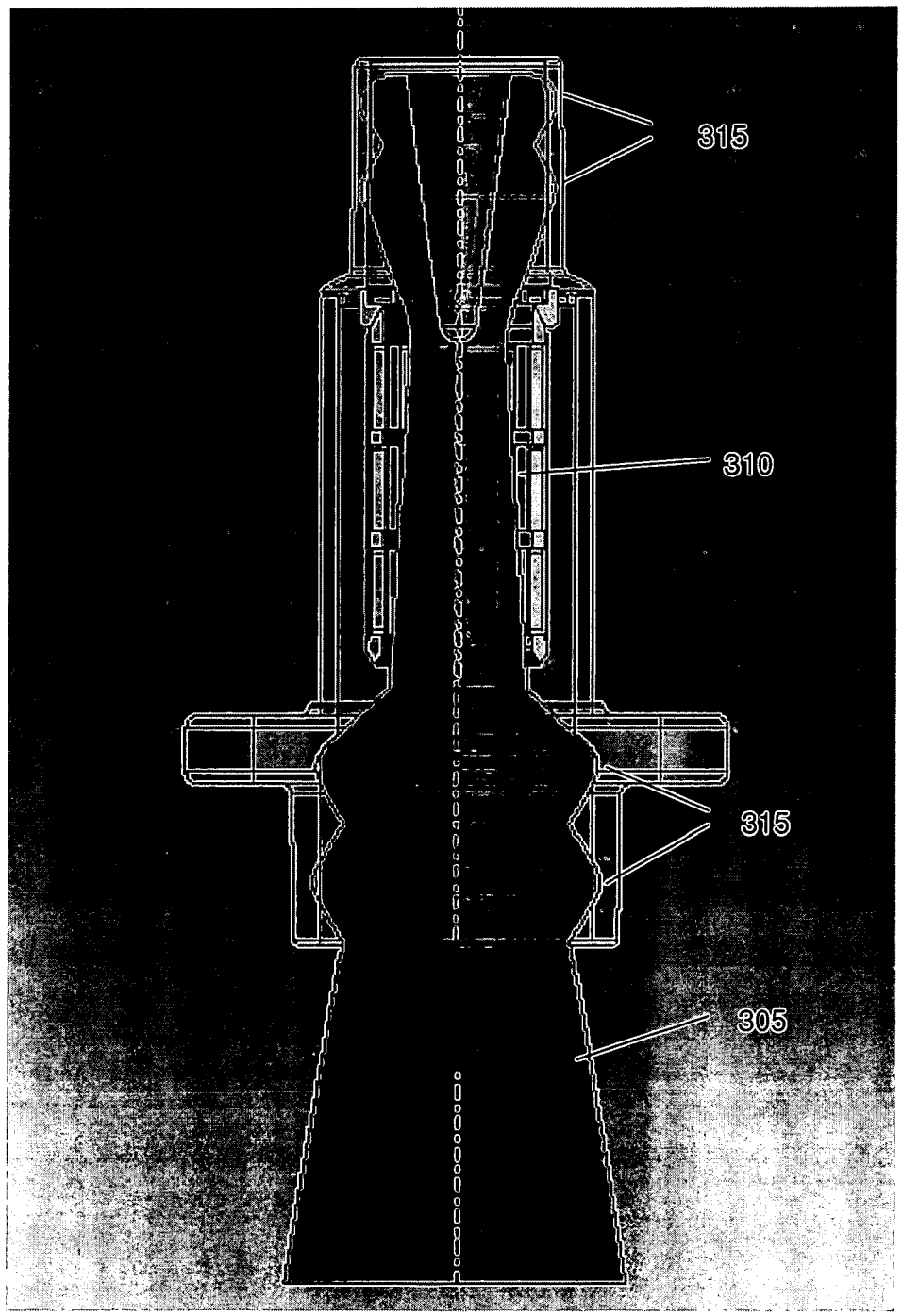
FIGS. 3A and 3B show diagrams of a $CO_2$ detector device with an internal plug sealing element in accordance with an embodiment of the present invention.

In another embodiment, the $CO_2$ indicator is selectively sealed from the remainder of the tracheal tube device by a barrier having a plug configuration, e.g., as shown in FIG. 3A. In FIG. 3A, the plug 305 fits inside the portion of the device containing the $CO_2$ indicator 310, and forms sealed areas 315 where there are points of contact with the inner diameter of the device both proximal and distal to the $CO_2$ indicator. The plug may be fabricated from a compliant material which, upon appropriate placement in the proximal region of the tube, secures the plug in place so as to selectively seal the indicator. As shown in the embodiment of FIG. 3A, the plug includes compliant ridges that exert a force against the inner surface of the tube and thereby secure the plug in place until it is removed during use. In this embodiment, the internal plug serves as a barrier between the $CO_2$ indicator and the atmosphere. In one embodiment, the sterilization barrier created by the plug can be integrated with the packaging of the tracheal tube device, such that the process of opening the package can include the removal of the internal plug.

Where the sterilization barrier has a plug configuration such as illustrated in FIG. 3A and described above, the barrier may be fabricated from a variety of different types of materials, so long as the material exhibits storage stability, compatibility with the other components of the device and the ability to serve as a sterilization barrier that prevents sterilizing components, e.g., gases, from reaching the indicator composition that is selectively sealed by the barrier and to keep the sterilized component sterile for the entire shelf life. Materials of interest include, but are not limited to, elastometric and polymeric materials. Suitable polymeric materials of interest include, but are not limited to: butyl rubber, mylar, Teflon, and the like.

Figure 3B:
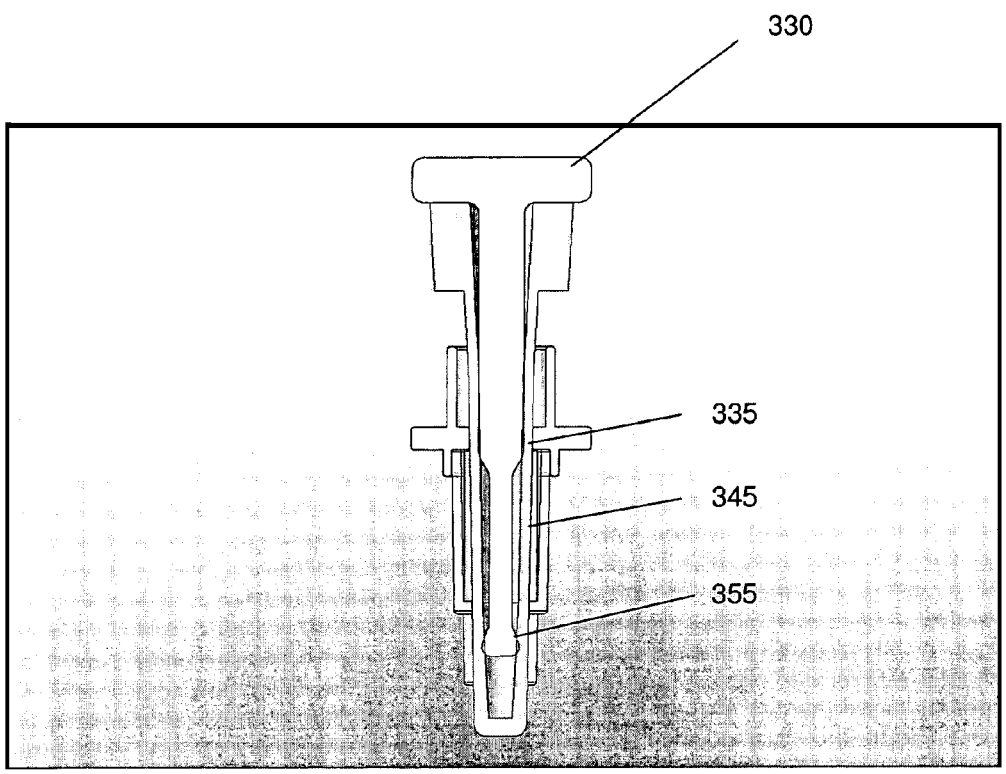

In certain embodiments, a separate element that maintains the plug in position may be employed. As seen in FIG. 3B, a plunger 330 is used to expand the plug radially against the inner diameter of the minor diameters 335 and 355 of the detector body to ensure a good seal. The plunger is stepped in such a way to allow for increased clearance 345 around the detector paper. The plunger may be glued into the plug to prevent dislodgement. To remove the plunger-plug assembly, the user simply pulls proximally on the head. In certain embodiments, the plug may have an integrated stylet element, e.g., to assist in placement of the tube. In these embodiments, the stylet element is employed to position the tube and, after positioning, is removed and removes the plug as well, thereby removing the sterlization barrier such that the device is ready for use.

In certain embodiments, the portion of the device containing the $CO_2$ indicator can have a divergent flow chamber, i.e., an inner lumen of varying diameters, which is designed to facilitate sealing of the $CO_2$ indicator with an internal plug (e.g., as illustrated in FIGS. 4A and B). FIG. 4B is an illustration of the device containing the $CO_2$ indicator, and FIG. 4A shows a cross-sectional view taken along line A-A of FIG. 4B. As shown in FIG. 4A, the proximal region of the device region that includes $CO_2$ indicator can have a smaller diameter 405 as compared with the diameter of the chamber where the $CO_2$ indicator 410 is housed 415. The chamber diameter then decreases to a smaller diameter distally 420. In certain embodiments, the diameter in region 415 is greater than the diameter of 420 and/or 405 by a factor of about 1.2 or more, such as 0.1 inches or more. The divergent flow chamber configuration allows the convenient formation of sealed areas where there are points of contact with the inner diameter of the device both proximal 405 and distal 420 to the $CO_2$ indicator.

By selectively sealing the $CO_2$ indicator with a sterilization barrier, e.g., a film of flexible sealing material or a plug, as shown in the embodiments of FIGS. 1-4, the tracheal tube and the $CO_2$ indicator can be packaged and sterilized as one integrated device. While not an aspect of all embodiments of the invention, in certain embodiments, the integrated tracheal tube device, including the removable sterilization barrier formed by the film or the plug, can be opened with one motion, saving valuable time in an emergency.

The $CO_2$ indicator portion of the device is continuous with the tracheal tube portion of the device in such a way that a continuous lumen is formed from one end of the device to the other, allowing the passage of a suction tube. The "in-line" design of the $CO_2$ indicator has the added benefit of a minimal amount of dead space, which can be important in maximizing the efficiency of gas exchange.

Figure 5A:
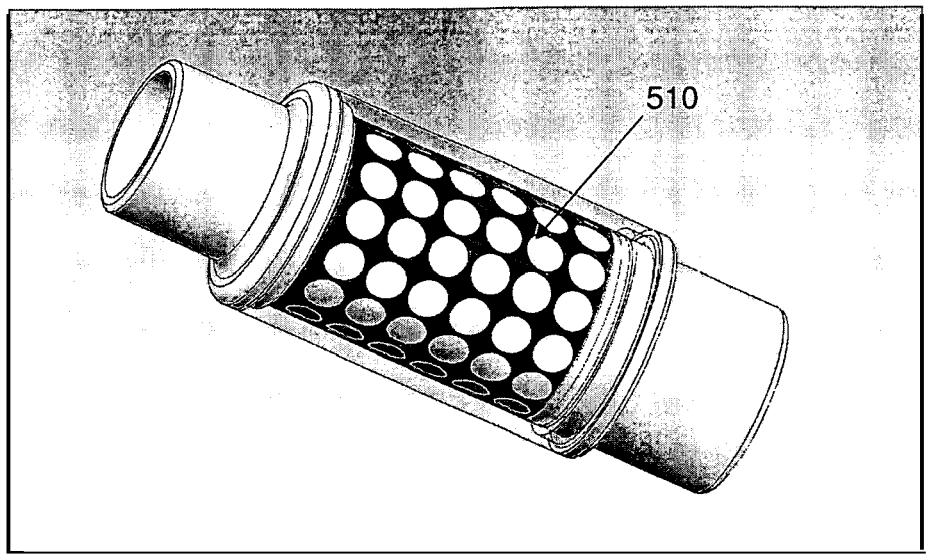
FIG. 5A shows a diagram of a $CO_2$ indicator having a patterned background in accordance with an embodiment of the present invention.
Figure 5B:
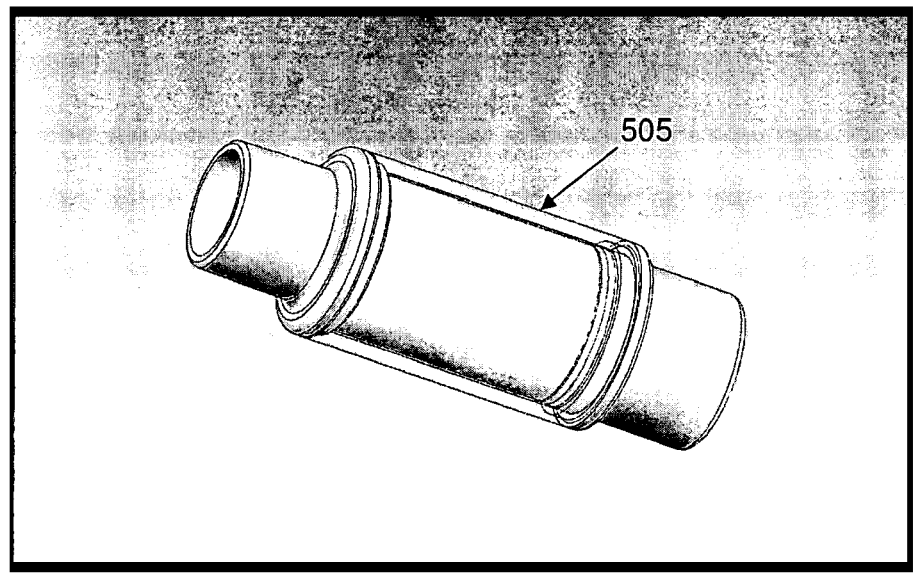
FIG. 5B shows a diagram of a $CO_2$ indicator window with an anti-glare coating found in embodiments of the present invention.
Figure 9A:
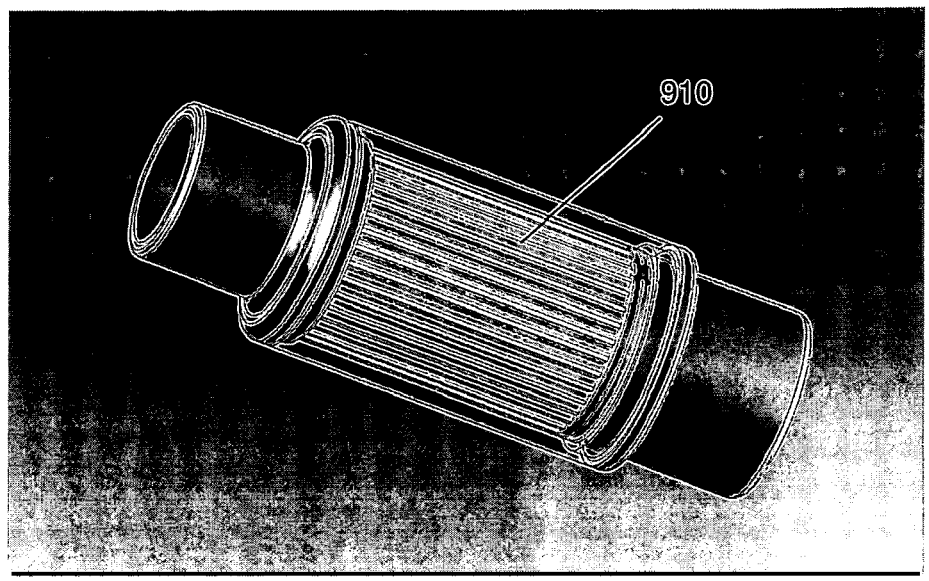
FIG. 9A shows a diagram of a $CO_2$ indicator having increased surface area in accordance with an embodiment of the present invention.
Figure 9B:
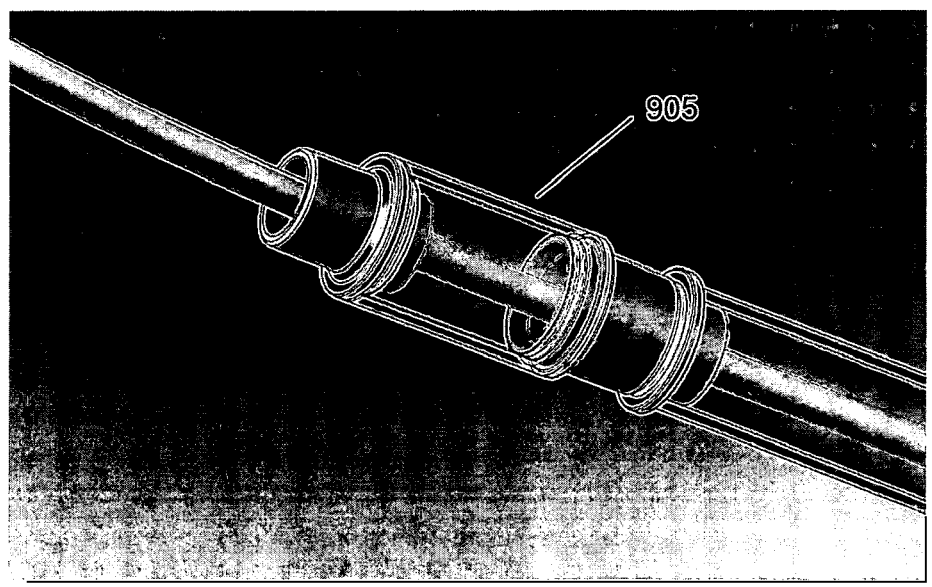
FIG. 9B shows a diagram of a $CO_2$ indicator having a transparent section in accordance with an embodiment of the present invention.

In one embodiment, the region of the device containing the $CO_2$ indicator can have a transparent portion, or window (element 505 in FIG. 5B and element 905 in FIG. 9B), for viewing of the $CO_2$ calorimetric indicator. To enhance visualization of the $CO_2$ indicator, in one embodiment the viewing window can be treated with an anti-glare coating, and in another embodiment the viewing window can have a matte finish (FIG. 5B). Other methods of visualization enhancement for the $CO_2$ indicator include enhanced contrast detection using patterns, e.g. a pattern against a contrasting background (element 510 in FIG. 5A). In certain embodiments, the pattern can comprise dots, stripes, or any other pattern that can demonstrate and increase the visibility of the color change of the calorimetric $CO_2$ indicator. The pattern can be produced by variations in treating the filter paper with the chemical reagents of the $CO_2$ indicator, the details of which are explained below. The pattern can be created by using by placing a 'mask' or a lattice, or any other desired pattern over the filter paper. The pattern can also be placed on the viewing window itself, as desired, and can be sprayed on, or stamped on, or placed on the viewing window by any other convenient method. The contrasting color background can be purple, or any other color that contrasts with the $CO_2$ indicator calorimetric paper.

Figure 6A:
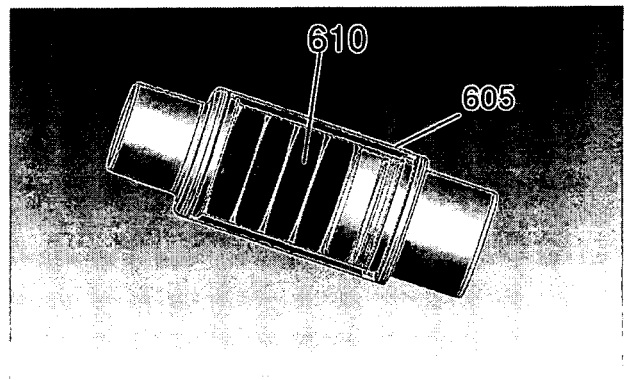
FIGS. 6A-C show a diagram of a $CO_2$ indicator configured to provide an indication of motion simulation in accordance with an embodiment of the present invention.
Figure 6B:
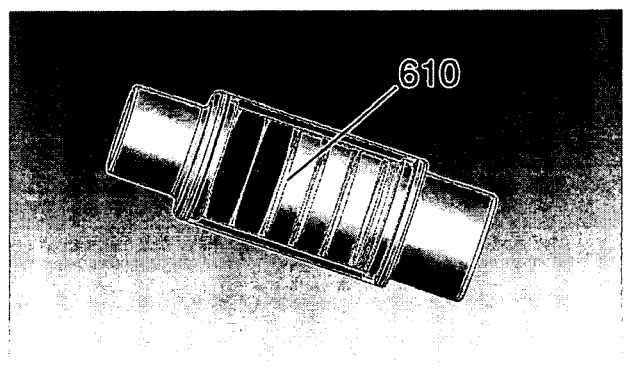
Figure 6C:
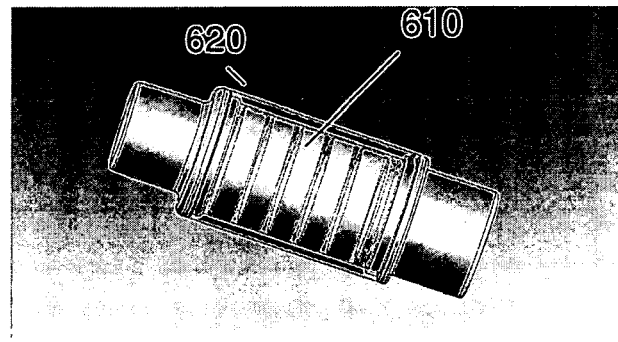

In other embodiments, visualization of the $CO_2$ indicator can be enhanced with the use of simulated motion or adjunctive motion of the detector, which in some embodiments can also indicate the direction of air flow. In FIGS. 6 A-C, a diagram of a $CO_2$ indicator is shown in which the $CO_2$ indicator paper 610 is cut into circular strips placed along the length of the viewing window. In this embodiment, the color change indicating exposure to a threshold level of $CO_2$ gas (e.g. the change from purple to yellow) progresses from the proximal 605 to the distal 620 portion of the indicator, in the direction of motion of expired air from a subject. In addition to providing an indication of the presence of $CO_2$ gas, this embodiment can also give the viewer a perception of movement, indicating the direction of air flow. In certain embodiments, the indicator paper can also be cut into a spiral configuration, or any other configuration convenient to demonstrate the direction of air flow.

Figure 7A:
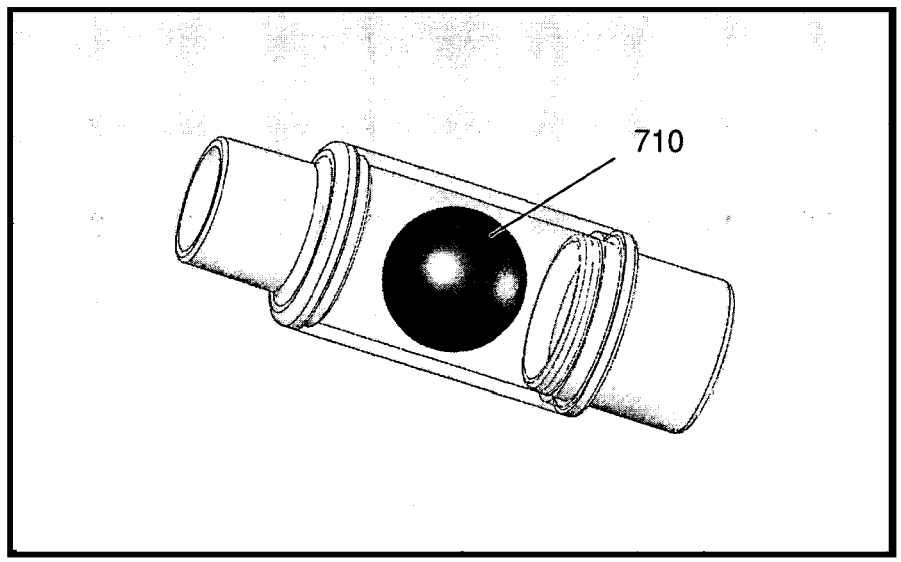
FIGS. 7A & B show a diagram of a $CO_2$ indicator configured to provide for adjunctive motion in accordance with an embodiment of the present invention.
Figure 7B:
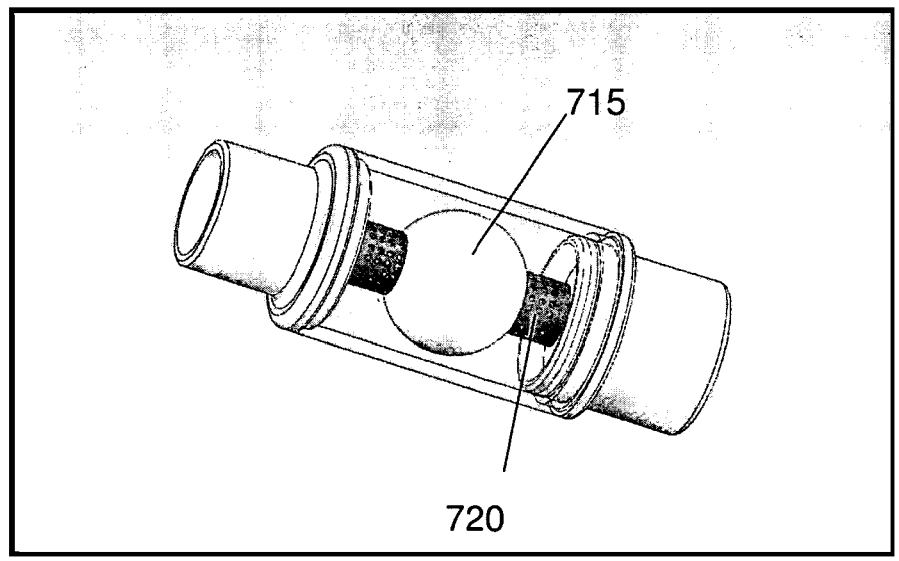

In another embodiment, visualization of the $CO_2$ indicator can be enhanced with the use of adjunctive motion of the detector. In some embodiments, physical motion of a portion of the detector can accompany the color change of the indicator. FIGS. 7A & B show an embodiment wherein the $CO_2$ indicator is in the shape of a sphere, formed by indicator filter paper 710 in FIG. 7A, and 715 in Fig. B. In the embodiment shown in FIG. 7A, the sphere is freely floating in the inner lumen of the $CO_2$ indicator chamber, and the motion of the sphere reflects the direction of the air flow (e.g. the sphere moves distally during exhalation, and moves proximally during inhalation). The sphere in this embodiment is of a dimension and weight sufficiently small and light so as not to impede air flow around the sphere, so that the sphere can float freely with inspiration and expiration. In this embodiment, the $CO_2$ indicator functions as in the previously described embodiments, such that the $CO_2$ indicator (the sphere in this example) can change from e.g. purple initially 710, to e.g. yellow 715 shown in FIG. 7B, after exposure to a threshold concentration of $CO_2$ gas. In one embodiment, the $CO_2$ indicator in the shape of a sphere is mounted on a central core with an internal lumen 720, which is continuous with the lumen of the tracheal tube device, allowing for the passage of a suction tube.

Figure 8:
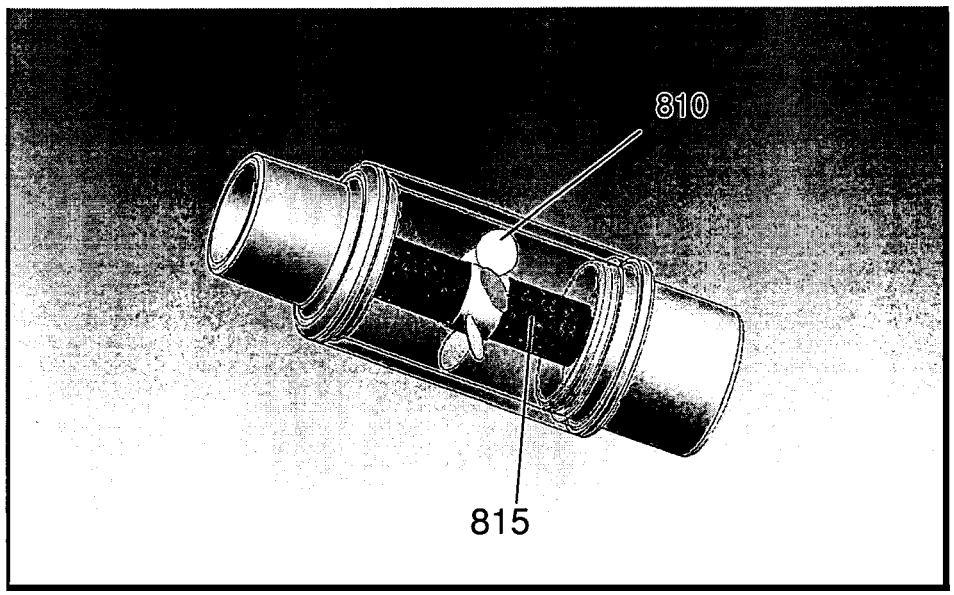
FIG. 8 shows a diagram of a $CO_2$ indicator having a propeller in accordance with an embodiment of the present invention.

In certain embodiments, the $CO_2$ indicator can be in any convenient shape, including but not limited to a semi- or hemi-sphere, a ring, a cylinder, or a propeller shape, as shown by element 810 in FIG. 8. In this embodiment, the $CO_2$ indicator is in the shape of a propeller, which in addition to exhibiting a color change associated with exposure to $CO_2$ gas, and proximal and distal motion associated with inspiration and expiration, can also rotate, or spin, in response to the air flow. The direction of the spin indicates the direction of the air flow. In this embodiment, the $CO_2$ indicator in a propeller shape is mounted on a central core with an internal lumen 815, which is continuous with the lumen of the tracheal tube device, which allows for the passage of a suction tube.

Aspects of the invention also include various features which increase the functionality and sensitivity of the $CO_2$ indicator, such as increased surface area of the indicator. The surface area of the $CO_2$ indicator is important for performance, in allowing a quick response time to a rapidly moving flow of $CO_2$ gas. Configurations of the $CO_2$ indicator such as an accordion shape, or a bellows (910 in FIG. 9A) can increase the surface area of the $CO_2$ indicator, and also allow maximum exposure to the $CO_2$ gas because of minimal contact with the inner lumen of the device. In this embodiment, the inherent spring force of the folded paper tightly secures the indicator paper against the inner lumen of the device.

Figure 10:
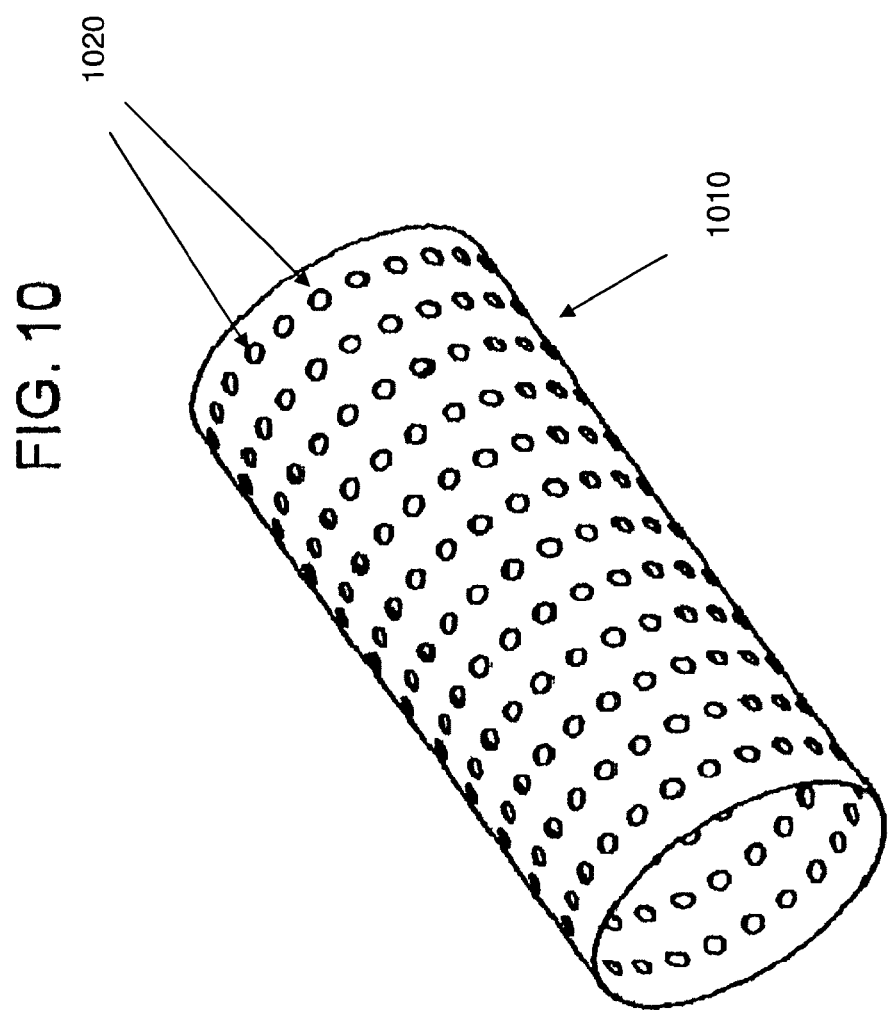
FIG. 10 shows a diagram of a $CO_2$ indicator having a perforated structure in accordance with an embodiment of the present invention.

Other embodiments of the invention which also increase the functionality and sensitivity of the $CO_2$ indicator include an embodiment in which the indicator paper 1010 is permeable or perforated (FIG. 10). Perforations 1020 such as those shown in the embodiment in FIG. 10 allow divergent or turbulent air flow around the perforations, which results in increased contact of $CO_2$ gas with the indicator, with air flow both inside and outside of the $CO_2$ indicator paper. In another embodiment, the indicator paper could be formed with a multitude of baffles, folds, or air scoops, in which the air flow is passed to the outside of the indicator paper.

In certain embodiments, the indicator may be present in a structure that protects the indicator paper from exposure to water vapor. For example, the indicator may be present in a structure that substantially reduces, if not eliminates, the possibility that water vapor present in the tube (e.g., from the patient's breath) will contact the indicator paper. As such, the indicator is present in a structure that inhibits the ability of water vapor to contact the indicator.

FIGS. 11A to 11D provide various views of an embodiment of the indicator which is present in a structure that protects the indicator from contact with water vapor. In the embodiment shown in FIGS. 11A to 11D, the indicator is part of a detector cartridge structure, where the indicator paper is present between an outer backing layer or barrier and a selective gas permeable inner layer that acts to protect the indicator from water vapor. The inner layer is a hydrophobic gas permeable barrier and the outer layer is a second barrier that includes a transparent region, e.g., for viewing the indicator. In the embodiment shown in FIGS. 11A to 11D, the detector cartridge comprises of a multitude of layers in the shape of a tube or a thin-walled extruded "C", where the structure is configured to be positioned inside of a tracheal tube in an in-line configuration. FIG. 11A provides a three-dimensional view of the tube configuration 1100 having an outer layer 1110 and an inner layer 1120. FIG. 11B provides a side view of the structure shown in FIG. 11A and FIG. 11C provides a cutaway view (scale 6:1) along line A-A of FIG. 11B.

FIG. 11D provides a detailed view of view "B" noted in FIG. 11C (scale 26:1). In FIG. 11D, the outer layer 1130 is comprised of a transparent and moisture blocking material such as polyethylene. An anti-fogging agent may be applied to this layer to prevent fogging, where such agents include, but are not limited to various silicone compounds. The thickness and material properties of the outer layer are chosen to provide a sufficient level of structural stiffness or radial force. In certain embodiments, the outer layer has a thickness ranging from 0.001 inches to 0.010 inches.

The next layer 1140 is a transparent mesh or spacing insert. This layer provides highly permeable spacing between the detector paper and the outer layer to increase gaseous flow through the detector paper. This layer may be made up of a variety of materials, such as but not limited to: polyester mesh, and the like. In certain embodiments, the mesh layer has a thickness ranging from 0.005 to 0.020 inches.

The next layer is the detector paper 1150. This detector paper may be any convenient detector, including the detector of the present invention described in greater detail below as well as any of the other detectors referenced herein.

The next layer 1160 is a desiccant. This layer is permeable to $CO_2$ but captures water vapor that passes through the inner layer. Suitable desiccants include, but are not limited to: ultra-fine silica suspended on a porous surface and the like. The thickness of this layer may vary, and in certain embodiments, range from 0.001" to 0.050".

The inner layer 1170 is a hydrophobic and gas permeable material, such as Tyvek™ or Goretex™. This layer provides two major functions. First, it protects the detector paper from condensed $H_2O$. Second, it entraps the chemistry contained on the paper within the cartridge thereby avoiding potential exposure to the patient.

Element 1180 in FIG. 11C is an inner-outer layer seal, where the inner and outer layers are sealed to each other to entrap the inner layers, e.g., by means of adhesive or hot sealing.

The structure shown in FIGS. 11A to 11D provides one or more advantages, including but not limited to: providing stiffness and structure to the paper, keeping the indicator in place, limiting chemicals from leaching out of the paper, and extending the lifetime of the indicator.

Additional embodiments of the present invention include the incorporation of an audible detector into the indicator paper, such that air flow over, around, or through the $CO_2$ indicator paper would create an audible indicator of air flow. Another embodiment of the invention includes the incorporation of an external device which can sense the change in color of the $CO_2$ indicator paper, such that a battery operated optical emitter/detector pair can convert the sensed color change to an audible signal. This device can be fitted over the outside of the $CO_2$ indicator portion of the device, and can be reusable.

In other embodiments, the $CO_2$ indicator could be viewable in the dark, with the inclusion of a small battery and a LED, which could be reusable. In another embodiment, the $CO_2$ indicator can include additional chemical agents which emit a distinctive smell upon detection of a threshold amount of $CO_2$ gas.

The $CO_2$ indicator portion of the device can also manufactured separately or in a way that can be detachable, for use with another tracheal tube, or for exchange of the $CO_2$ indicator.

Aspects of the invention include methods of making the tracheal tube device as described above. The tracheal tube portion of the device can be manufactured from any medically suitable material, such as a medical grade plastic or silicone material, or in some embodiments metal, in which the tubular structure can be formed by any convenient method, including but not limited to, placing the medical-grade material in a mold, or injection mold, or by machining or milling a preformed tube to the desired configuration. The proximal region of the tubular structure can have a region for placement of the $CO_2$ indicator paper as described in the above embodiments. In one embodiment, the tracheal tube device can also include a chamber of varying diameter, as described in FIG. 4, above. In another embodiment, the tracheal tube device can also include a clear, or transparent viewing portion around the region of the $CO_2$ indicator, as described above. The distal region of the tracheal tube device can be formed for placement into a subject's trachea, and can be tapered or sized to fit a variety of subjects (e.g. a smaller diameter distal tube for insertion into pediatric patients). In some embodiments, the distal region of the device can be formed for placement into a subject's pharynx, and can be tapered or sized to fit a variety of subjects. The tracheal tube device can also comprise a cuff, for sealing and securing the distal end of the tube in the subject, either in the trachea, or in the pharnynx, as with a laryngeo-pharyngeal airway.

The $CO_2$ indicator portion of the invention can also be made as a separate unit, using a similar process as described above, so that the $CO_2$ indicator portion is detachable for use with another tracheal tube, or for exchange of the $CO_2$ indicator. In this embodiment, the distal end of the $CO_2$ indicator portion can be tapered or sized to fit a variety of tracheal tubes, as can be used with different sized subjects (e.g. a smaller diameter for pediatric patients).

Long Lasting, Rapid Response $CO_2$ Indicator

Aspects of the invention include a long lasting $CO_2$ indicator that exhibits a dynamic, rapid response reversible $CO_2$ indication with breath-to-breath sensitivity and is storage stable. The calorimetric $CO_2$ indicator of embodiments of the invention changes color upon exposure to changes in concentrations of $CO_2$ found in expired air (e.g. from purple to yellow). In certain embodiments, the $CO_2$ indicator can change color, e.g. from purple to yellow, in 2.5 seconds or less, such as 2 seconds or less and including 0.75 seconds or less in response to a change in $CO_2$ concentration in a gas contacting the indicator. The indicator is sensitive to changes in $CO_2$ concentration of 3% or less, such as 2% or less, including 1% or less. At $CO_2$ concentrations of 0.05% or less, such as 0.03% or less, the indicator is a first color, while at concentrations above these amounts, the indicator is a second color. For example, in certain embodiments, the indicator exhibits the following colors at the following $CO_2$ concentrations: <0.03%, purple; 0.5% light purple; 2% brownish yellow; 5% yellow. The color change can be any of a variety of different color changes, e.g., purple to yellow, blue to yellow, red to yellow, orange to yellow, etc.

As reviewed above, the indicator of the invention is long lasting. By "long lasting" is meant that the indicator exhibits, in certain aspects, long life, such that it can continue to respond to changes in $CO_2$ concentration under conditions of active use for a period of 0.5 hours or longer, such as 1 hour or longer, including 2 hours or longer, where the indicator may retain functionality under conditions of continuous use for priods of 4 hours or longer, such as 6 hours or longer, including 12 hours or longer, e.g., 24 hours or longer.

Certain embodiments of the $CO_2$ indicator of the present invention exhibits storage stability, by which is meant that the indicator composition may be maintained for a period of about 6 months or longer, such as 1 year or longer, without suffering any negative impact in terms of performance capability, e.g., as described above.

Aspects of the invention include the combination of various components in a concentration and ratio sufficient to provide a dynamic, rapid response reversible $CO_2$ indicator with breath-to-breath sensitivity, e.g., as described above. In one embodiment, the components of the $CO_2$ indicator include a pH sensitive indicator dye(s) and a phase transport enhancer.

pH sensitive indicator dyes of interest include, but are not limited to: bromothymol blue, phenolphthalein, thymol blue, phenol red, rosolic acid, m-nitrophenol, xylenol blue, curcumin, cresolphthalein, thymolphthalein, malachite green, N,N-dimethylaniline, and cresol dyes, e.g., bromcresol green, bromocresol purple, cresol red, m-cresol purple, etc. In certain embodiments, the pH sensitive indicator dye is a cresol dye or combination thereof, e.g., a combination of m-cresol purple and cresol red, such as the combination described in the working exemplification below.

In addition, the pH sensitive indicator dye, another component present in the indicator of the invention is a phase transport enhancer. Phase transport enhancers contained as part of the dye solution applied to the support surface, enhance response of the dye to $CO_2$ gas as well as alter the color and visibility of the indicator. Phase transport enhancers include, but are not limited to: quaternary ammonium, phosphonium or pyridinium salts. Quaternary salts which are useful in the practice of the invention have the formula (I):

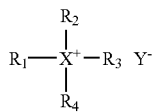

wherein:
X=N or P;
$R_1$, $R_2$, $R_3$ and $R_4$ are selected from the group consisting of $C_1$-$C_{16}$, such as $C_1$-$C_{12}$ alkyl, triphenylmethyl, phenyl, naphthyl and benzyl, $C_1$-$C_4$ substituted alkyl wherein the substituent is a $C_1$-$C_4$ alkyl or phenyl group, wherein $R_1$, $R_2$, $R_3$ and $R_4$ may be the same or different, e.g., have the same or different number of carbon atoms; and
$Y^-$ is an anion selected from the group consisting of hydroxide, fluoride, chloride, bromide, iodide, carbonate and tetrafluoroborate.

Phase transport enhancers which are useful in the practice of the invention include, but are not limited to: tetrabutylammonium hydroxide; tetrabutylammonium chloride; tetraethylammonium bromide; tetraethylammonium p-toluenesulphonate; phenyltrimethylammonium chloride; benzyltrimethylammonium bromide; tetra-n-propylammonium bromide; benzyltriethylammonium tetrafluoroborate; n-Dodecyltrimethylammonium bromide; tetraphenylphosphonium chloride; n-Hexadecylpyridinium bromide; and (Triphenylmethyl)triphenyl phosphonium chloride.

The subject invention can be produced by combining the various components of the indicator composition to produce a precursor indicator reagent fluid and then contacting the fluid with a suitable solid support in a manner sufficient to produce the desired indicator composition. In certain embodiments, the precursor fluid is an aqueous solution, such as a basic aqueous solution, that includes the above described pH sensitive dye and phase transport components. The basic solution has, in certain embodiments, a pH ranging from 10 to 12.5 The composition may include one or combination of pH sensitive indicator dyes. In certain embodiments, the composition includes more than one pH sensitive indicator dyes, such as 2 to 5 different dyes, e.g., 2 to 4 different dyes, including 2 to 3 different dyes, e.g., 2 different dyes. In certain embodiments, the dyes are cresol dyes, such as 2 different cresol dyes. When the composition includes two different pH sensitive indicator dyes, the pH sensitive indicator dyes can be present in a concentration ranging from 0.0001 Molar to 0.01 Molar, including about 0.002 Molar to 0.003 Molar. In certain embodiments, the dyes are m-Cresol purple and cresol red. M-cresol purple can be present in the reagent fluid in a concentration ranging from 0.001 Molar to 0.01 Molar, including about 0.002 Molar to 0.003 Molar. Cresol red sodium salt can be present in reagent fluid in a concentration ranging from 0.0001 Molar to 0.001 Molar, including about 0.002 Molar to 0.003 Molar. The concentration of phase transport enhancer may vary. In certain embodiments, the amount of phase transport enhancer present in the reagent fluid ranges from 0.001 Molar to 0.02 Molar, such as from 0.005 Molar to 0.01 Molar.

Following preparation of the precursor fluid, the methods include contacting the fluid with a solid support, and then removing excess fluid from the solid support to produce the indicator. Any convenient solid support may be employed. In certain embodiments, the solid support is a flexible solid support (e.g. a cellulosic material), e.g., paper. In certain embodiments, the solid support may be a filter paper, e.g., having a porosity ranging from 1 µm to about 60 µm, such as from 20 µm to about 30 µm. The solid support can be a material dimensioned to fit inside the tracheal tube device, in any of the embodiments described above. The support of the $CO_2$ indicator can be shaped into any desired configuration, including but not limited to: circular or spiral strips, a sphere or portion of a sphere, a propeller, an accordion shape, etc. The support of the indicator can further comprise a pattern, and/or can have perforations, as described in the above embodiments.

The above described indicators can be used in any of a number of different devices, including tracheal tube devices. For example, the above indicators may find use in the tracheal tube devices described in U.S. Pat. Nos. 4,728,499; 4,879, 999; 4,994,117; 5,005,572; 5,156,159; 5,166,075; 5,179,002; 6,436,347; 6,584,974; and U.S. Patent Application Publication No. 2006/02168282; the disclosures of which with respect to tracheal tube devices are herein incorporated by reference. In certain embodiments, the indicators are employed in the tracheal tube devices of the present application, e.g., as described in the preceding section. In certain embodiments, the indicators are employed with tracheal tube devices that do not include a sterilization barrier, as the indicator of such embodiments can survive the sterilization, e.g., EtO, process.

Methods of Using

The present invention provides a method of placing a tracheal tube having an integrated calorimetric $CO_2$ indicator within a subject, which can be used in a variety of applications. The subject methods may be used in a variety of subjects, including humans, e.g., as described above. In certain embodiments, the subjects or patients are humans, ranging from neonates to adults. The subject methods are useful in any situation in which access is needed to the airway of a subject or patient; in some embodiments this is accomplished using an endotracheal tube placed into the trachea via the mouth, in other embodiments a nasotracheal tube is placed into the trachea through the nose, or a tracheostomy tube is placed into the trachea through a tracheostomy opening. In some embodiments, the device is a laryngeo-pharyngeal airway (LPA) which is placed in the pharnyx above the larynx. A tracheal tube device with $CO_2$ detection capability is important when attempting to confirm the proper placement of an tracheal tube in the airway of a patient, especially in an emergency situation, when it is likely that less skilled personnel are available. The ability to sterilize and package a tracheal tube device with a $CO_2$ indicator that is storage stable, with packaging that can be opened easily (including embodiments where the packaging can be opened with one motion is important for emergent placement of a tracheal tube when time is critical.

The method of inserting an endotracheal tube into a subject involves the steps of: obtaining a pre-assembled and sterilized endotracheal tube with an integrated calorimetric $CO_2$ indicator in a package; opening the endotracheal tube system by removing the outer packaging, either with or without associated removal of the sterilization barrier; removing the sterilization barrier if not removed as part of opening the package; inserting the laryngoscope in the subject's mouth to find the trachea; inserting the pre-assembled endotracheal tube into the subject; ventilating the patient; determining proper placement of the endotracheal tube within the subject's trachea by observing the carbon dioxide indicator for color change; if the indicator does not show a color change (e.g. from purple to yellow) associated with $CO_2$ in expired air from the subject's lungs, then reposition the tracheal tube until the desired color change is observed, indicating correct placement of the endotracheal tube.

Kits

As summarized above, also provided are kits comprising the tracheal tube device and/or indicator of the subject invention.

In certain embodiments of the subject kits, the kits can include a tracheal tube device containing a $CO_2$ indicator, and can further include instructions for using the subject device or elements for obtaining the same (e.g., a website URL directing the user to a webpage which provides the instructions), where these instructions are typically printed on a substrate, which substrate may be one or more of: a package insert, or the packaging, and the like. The kit can also comprise the $CO_2$ indicator portion of the device, for use with other tracheal tubes. The kit may also include a stylet, or a laryngoscope for use in insertion of the tracheal tube, and/or also include a suction tube, with instructions for using, or elements for obtaining the same, which can be placed through both the tracheal tube portion of the device and the $CO_2$ indicator portion of the device. In certain embodiments, e.g., as described above, the stylet may be part of the device, e.g., joined to the plug, such that the plug is configured to include a stylet element.

The following example is provided by way of illustration and not by way of limitation.

Experimental 16 ml aqueous solution of pH 11.2 NaOH and 4 ml aqueous solution of pH 11.4 $Ca(OH)_2$ are combined with mixing in a 50 ml beaker. 1.6 mg of m-cresol purple sodium salt and 0.1 mg of cresol red sodium salt are then dissolved into the solution. Next, 8 ml of Propylene Glycol and 2 ml of Glycerol are transferred into the above solution. 100 µl TBAH is then transferred into the solution and mixed thoroughly. The final pH of this solution should be in the range of 11.15 to 11.35.

Filter paper is then immersed into this final mixed solution for one minute, following which the filter paper is removed with flat tip tweezers and placed onto dry clean kimwipes to remove excess fluid.

The resultant detector paper is then dried by maintaining it in the presence of Drierite (Anhydrous Calcium Sulfate) under an $N_2$ filled Zip lock bag and flushed the bag with $N_2$ atmosphere for at least 24 hours before use.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A tracheal tube device comprising:
   a) an elongated tubular element having:
      i) a distal region configured for placement to access the trachea of a subject;
      ii) a proximal region, wherein the distal region and the proximal region are portions of the same elongated tubular element; and
      iii) a longitudinal axis extending from the distal region to the proximal region;
   b) a $CO_2$ indicator present on an inner surface of said elongated tubular element at said proximal region and integrated into the tubular element; and
   c) a removable sterilization barrier, wherein the removable sterilization barrier is a film that has a major extension from a proximal end to a distal end of the $CO_2$ indicator along the longitudinal axis and selectively seals the $CO_2$ indicator from the remainder of the tracheal tube device and is configured to be removed from the tracheal tube device before the device is used to intubate a subject without removing the $CO_2$ indicator.

2. The tracheal tube device according to claim 1, wherein said film covers inner and outer surfaces of said proximal region of said elongated tubular element.

3. The tracheal tube device according to claim 1, wherein said $CO_2$ indicator comprises a $CO_2$ sensitive chemical reagent present on a solid support.

4. The tracheal tube device according to claim 3, wherein said solid support is a flexible solid support.

5. The tracheal tube device according to claim 4, wherein said flexible solid support comprises a cellulosic material.

6. The tracheal tube device according to claim 4, wherein said solid support is configured as a tube dimensioned to fit inside of said elongated tubular element at said proximal region.

7. The tracheal tube device according to claim 1, wherein said $CO_2$ indicator exhibits breath to breath dynamic color change.

8. The tracheal tube device according to claim 1, wherein said $CO_2$ indicator is storage stable.

9. The tracheal tube device according to claim 1, wherein all of said device but said $CO_2$ indicator has been sterilized.

10. The tracheal tube device according to claim 1, wherein said $CO_2$ indicator is a long lasting rapid response reversible $CO_2$ indicator that exhibits breath to breath dynamic color change.

11. The tracheal tube device according to claim 10, wherein said $CO_2$ indicator comprises a $CO_2$ sensitive chemical reagent present on a solid support.

12. The tracheal tube device according to claim 11, wherein said solid support is a flexible solid support.

13. The tracheal tube device according to claim 12, wherein said flexible solid support comprises a cellulosic material.

14. The tracheal tube device according to claim 13, wherein said solid support is configured as a tube dimensioned to fit inside of the elongated tubular element at a proximal region thereof.

15. The tracheal tube device according to claim 11, wherein said chemical reagent comprises a pH sensitive indicator dye.

16. The tracheal tube device according to claim 15, wherein said pH sensitive indicator dye comprises a cresol.

17. The tracheal tube device according to claim 16, wherein said dye comprises first and second cresols.

18. The tracheal tube device according to claim 17, wherein said first cresol is m-cresol purple and said second cresol is cresol red.

19. The tracheal tube device according to claim 11, wherein said chemical reagent further comprises a phase transport enhancer.

20. The tracheal tube device according to claim 19, wherein said phase transport enhancer is a quaternary ammonium compound.

21. The tracheal tube device according to claim 20, wherein said cationic quaternary ammonium compound is TBAH.

22. The tracheal tube device according to claim 1, wherein the $CO_2$ indicator is positioned between a first hydrophobic gas permeable barrier and a second transparent barrier.

23. The tracheal tube device according to claim 1, wherein the removable sterilization barrier is configured to prevent a sterilization component from reaching the $CO_2$ indicator that is selectively sealed by the barrier.

24. The tracheal tube device according to claim 23, wherein the sterilization component is a gas.

25. The tracheal tube device according to claim 24, wherein the gas is ethylene oxide.

26. The tracheal tube device according to claim 1, wherein the removable sterilization barrier comprises butyl rubber, polyethylene terephthalate, or polytetrafluoroethylene.

27. The tracheal tube device according to claim 1, wherein the removable sterilization barrier is configured to be removed from the tracheal tube device in a single motion when the tracheal tube device is removed from a sterile package.

28. The tracheal tube device according to claim 27, wherein the removable sterilization barrier and the sterile package are formed as one unit.

* * * * *